United States Patent [19]

Jovanovics et al.

[11] 4,070,358
[45] Jan. 24, 1978

[54] PROCESS FOR THE PREPARATION OF DIINDOLE ALKALOIDS OR OF THE ACID ADDITION SALTS THEREOF

[75] Inventors: Karola Jovanovics; Kalman Szasz; Csaba Lörincz; Laszlo Hermann; Eszter Dezseri, all of Budapest, Hungary

[73] Assignee: Richter Gedeon Vegyeszeti Gyar Rt, Budapest, Hungary

[21] Appl. No.: 735,004

[22] Filed: Oct. 22, 1976

[30] Foreign Application Priority Data

Oct. 28, 1975  Hungary ................. RI 581

[51] Int. Cl.$^2$ ............................ C07D 519/04
[52] U.S. Cl. ........................................... 260/287 B
[58] Field of Search ................................ 260/287 B

[56] References Cited

U.S. PATENT DOCUMENTS

| 3,097,137 | 7/1963 | Beer et al. ............... 260/287 B |
| 3,225,030 | 12/1965 | Svoboda ................. 260/287 B |
| 3,944,554 | 3/1976 | Tafur ..................... 260/287 B |

FOREIGN PATENT DOCUMENTS 1,382,460  1/1975  United Kingdom .......... 260/287 B

*Primary Examiner*—Raymond V. Rush
*Assistant Examiner*—David E. Wheeler
*Attorney, Agent, or Firm*—Karl F. Ross

[57] ABSTRACT

A process is disclosed for the separation and recovery of vinblastine and leurosine from a mixture of diindole alkaloids obtained by extraction of the plant, *Vinca rosea* L.

6 Claims, No Drawings

PROCESS FOR THE PREPARATION OF DIINDOLE ALKALOIDS OR OF THE ACID ADDITION SALTS THEREOF

The invention relates to a process for the separation of diindole alkaloids or of the acid addition salts thereof; more particularly, the invention is a process for the separation of the two alkaloids vinleurosine (hereinafter: leurosine) and vincaleukoblastine (hereinafter: vinblastine) from the enriched mixture of the diindole alkaloids or acid addition salts, preferably sulfate salts thereof, obtained by extraction of the plant *Vinca rosea* L., or (by the other accepted name) *Catharantus roseus* G. Don.

The alkaloids leurosine, vinblastine and vincristine are known compounds, which are widely used in therapy as cytostatic agents. It is, therefore, a permanent intention of research workers to find always more effective processes for the recovery of the said alkaloids from the plant (cf. U.S. Pat. Nos. 3,097,137 and 3,205,220; Hungarian Pat. Nos. 153,200 and 154,715). The processes described in these patent specifications have the common characteristic feature that the separation of the about 80 indole alkaloids obtained by extraction of the plant is performed by various phase-changes (transfer of the alkaloids from organic phases into aqueous phases and vice versa) followed by adsorption chromatography.

The Hungarian Pat. No. 160,967 describes a process for the separation of the three diindole alkaloids leurosine, vinblastine and vincristine in the form of their acid addition salts, preferably sulfates, from the alkaloid mixture obtained by extraction of the plant and removal of the accompanying contaminants present in the extract. By this process the content of the said three diindole alkaloids in the crude alkaloid mixture can be enriched to 70–80%, and then only this crude mixture enriched in diindole alkaloids must be separated further by column chromatography.

Among the three diindole alkaloids mentioned above the vincristine is most valuable from the therapeutic point of view. The Hungarian Pat. No. 165,599 describes a process for the semi-synthetic preparation of vincristine by selective oxidation of vinblastine. In this way the vinblastine, which is therapeutically valuable in itself, is even more important as a starting substance for the preparation of vincristine. The plant *Vinca rosea* L. contains ten times more vinblastine than vincristine, and this relatively abundant substance can be now converted in a simple way and with very good yields into the very valuable cytostatic agent vincristine.

Also the importance of leurosine increased in the recent times by the recognition that this substance can be converted by oxidation into the new product N-formyl leurosine; this compound shows a considerable inhibiting effect against various types of tumours, e.g. Harding-Passey melanoma, VX epithelioma of rabbits, induced and transplanted rhabdomyo-sarcome, which could not be influenced by the cytostatic agents known and used hitherto, including also vinblastine and vincristine (see Hungarian Pat. No. 165,986).

The present invention provides a more effective method for the separation of the above described mixture of the acid addition salts of diindole alkaloids; this method eliminates the use of adsorption chromatography and yields vinblastine in a high purity which can be converted directly into vincristine by the said selective oxidation process. Also the other diindole alkaloids present in the said mixture can be separated and recovered by the method of the present invention.

It has been found that if, in a solution of a mixture of the acid addition salts of diindole alkaloids, the alkaloid bases are liberated by adding an organic base to the solution approximately 90 to 95% of the leurosine precipitates in the form of free base from the said solution. If this crude leurosine base is then separated by filtration and the filtrate is evaporated to dryness, the other diindole alkaloid bases can be separated by extraction with hydrocarbon-type solvents from the acid addition salt of the base used for setting free the alkaloids. The thus extracted alkaloid bases can be transferred into an aqueous phase by extracting the organic solution with a phosphate buffer solution having a pH-value of 3.7 to 4.3. From this aqueous solution the vinblastine can be separated selectively by readjusting its pH-value to 3.5 to 4.1 and extracting the aqueous phase with chlorinated hydrocarbon solvents; the vinblastine goes selectively into the organic phase, while the other diindole alkaloids remain in the aqueous solution.

Accordingly, the subject matter of the invention is a process for separating the diindole alkaloids from enriched mixtures thereof, which comprises dissolving the mixture of the acid-addition salts, preferably sulfates in an organic solvent at least partially miscible with water, preferably in an alcohol, adding to the said solution an organic base of higher basicity than the diindole alkaloids, separating the precipitated leurosine, evaporating the mother liquor to dryness, extracting the dry residue with a hydrocarbon-type solvent, preferably with benzene, extracting the obtained organic solution with an aqueous phosphate buffer solution having a pH-value of 3.7 to 4.3, preferably 4.0±0.1, readjusting the separated aqueous phase with phosphoric acid to pH 3.5 to 4.1, preferably 4.0±0.1, extracting the acidic aqueous phase with a chlorinated hydrocarbon solvent, preferably with dichloromethane and recovering the vinblastine base from the separated organic phase.

In a preferred practical performance of the process of the invention, the mixture of the acid addition salts, preferably sulfates of the diindole alkaloids is dissolved in a water-miscible solvent, as acetone or a lower aliphatic alcohol, e.g. methanol, ethanol, propanol or isopropanol. The dissolving is performed at a temperature between 0° and 50° C, preferably at room temperature. 3 to 10 parts by weight, preferably 4 to 8 parts by weight of the solvents are used to one part by weight of the mixture of the salts of the alkaloids.

The diindole alkaloid bases are then liberated in the solution by adding an organic base e.g. monomethyl amine, diethyl amine or pyridine. The said organic base is used in an equivalent amount (calculated on the acid mixture) or in a slight excess. The leurosine base separates precipitates from the solution at 0° to 25° C; the precipitation can be made more complete by cooling the solution to about 0° C. The precipitated leurosine is then filtered off, washed with the same solvent as used to the dissolution of the alkaloid salts, and then dried. The thus obtained crude leurosine may be purified in a per se known manner, e.g. by recrystallisation. If desired, the leurosine base can be converted into an acid addition salt, preferably into the sulfate salt. The acid addition salt may be prepared in known manner, e.g. by adding to the ethanolic solution of the leurosine anhydrous ethanol containing 0.5 per cent by volume sulfuric acid until reaching a pH-value of about 4.

The mother liquor obtained after the separation of leurosine is then evaporated to dryness under reduced pressure. The evaporation residue is dissolved in an organic solvent, preferably in a hydrocarbon of the benzene series, e.g. in benzene, toluene or xylene. The corresponding acid addition salt of the organic base (monomethyl amine, diethyl amine or pyridine) used for setting free the diindole alkaloid bases remains undissolved and is removed; the obtained organic solution is then extracted repeatedly with an aqueous phosphate buffer solution having a pH-value of 3.7 to 4.3, preferably 4.0±0.1. The pH-value of the combined aqueous extracts is readjusted with an acid, preferably with phosphoric acid to 3.5 to 4.1, preferably to 4.0±0.1. The thus obtained aqueous acid solution is then extracted with a chlorinated hydrocarbon, preferably with dichloromethane. The organic extracts are combined, dried over anhydrous sodium sulfate and evaporated to dryness under reduced pressure Vinblastine is obtained as an evaporation residue; this product may be converted, if desired, into an acid addition salt, preferably into the sulfate salt. The vinblastine sulfate obtained in this way can be used directly, without further purification, as starting material for the preparation of vincristine.

Further details of the process of the invention are illustrated by the following example; the invention is, however, by no means limited to the contents of this example.

EXAMPLE 50 g. of a crude mixture of diindole alkaloid sulfates are dissolved in 300 ml. of methanol and 13 ml. diethyl amine are added to the stirred solution. The solution is kept at 0° C for an hour; during this time the crude leurosine base crystallizes. The crystals are filtered off, washed with a small amount of methanol and dried in vacuo. 6.4 g. of crude leurosine base are obtained; this product contains 90 to 95 per cent of the leurosine originally present in the starting crude mixture of diindole alkaloid sulfates.

The obtained crude leurosine base is purified by recrystallisation from methanol; it can be converted, if desired, in the usual way into the sulfate addition salt.

The filtrate obtained after the separation of the crude leurosine base is evaporated to dryness and the evaporation residue is dissolved in 2500 ml. of benzene. The precipitated crystalline diethyl amine sulfate is filtered off, washed with a small amount of benzene. The diethyl amine may be recovered from this by-product.

The benzene solution obtained as filtrate is extracted three times with 2500 ml. each of an aqueous phosphate buffer solution having a pH-value of 4.0±0.1. This aqueous phosphate buffer solution is prepared by dissolving 10 per cent by weight of anhydrous sodium dihydrophosphate in water, and then adjusting the pH-value of the solution to 4.0±0.1 with aqueous N-phosphoric acid solution.

After the extraction the phases are separated and the aqueous phases are combined. The pH-value of this aqueous solution is re-adjusted to 4.0±0.1 and the aqueous solution is extracted with four portions of 2500 ml. each of dichloro methane. The dichloro methane phases are combined, dried over anhydrous sodium sulfate and evaporated to dryness under reduced pressure.

25 g. of vinblastine are obtained; this product can be used without further purification as starting material for the semi-synthetic preparation of vincristine.

The obtained 25 g. of vinblastine are dissolved in 80 ml. of methanol and the pH-value of this solution is adjusted to 5 by adding a 0.3 per cent by volume solution of sulfuric acid in ethanol. The mixture is allowed to stand; the vinblastine sulfate crystallizes from the solution.

What we claim is:

1. A process for isolating vinblastine from a mixture of diindole alkaloids comprising acid addition salts of vinblastine and leurosine which comprises the steps of:
   a. dissolving the mixture in an organic solvent at least partially miscible with water;
   b. adding to the solution formed in step (a) an organic base of higher basicity than that of vinblastine or leurosine;
   c. separating the precipitated leurosine;
   d. evaporating the remaining solution to leave behind a dry residue;
   e. extracting the dry residue formed in step (d) with a hydrocarbon solvent;
   f. extracting the solution formed in step (e) with an aqueous phosphate buffer solution having a pH of 3.7 to 4.3;
   g. readjusting the aqueous phase extracted in step (f) with phosphoric acid to a pH of 3.5 to 4.1;
   h. extracting the acidic aqueous phase formed in step (g) with a chlorinated hydrocarbon solvent; and
   i. recovering vinblastine from the chlorinated hydrocarbon solvent.

2. A process for isolating vinblastine from a mixture of diindole alkaloids comprising acid addition salts of vinblastine and leurosine which comprises the steps of:
   a. dissolving the mixture in an organic solvent at least partially miscible with water;
   b. adding to the solution formed in step (a) an organic base selected from the group consisting of monoethylamine, diethylamine and pyridine;
   c. separating the precipitated leurosine;
   d. evaporating the remaining solution to leave behind a dry residue;
   e. extracting the dry residue formed in step (d) with a hydrocarbon solvent;
   f. extracting the solution formed in step (e) with an aqueous phosphate buffer solution having a pH of 3.7 to 4.3;
   g. readjusting the aqueous phase extracted in step (f) with phosphoric acid to a pH from 3.5 to 4.1;
   h. extracting the acidic aqueous phase formed in step (g) with a chlorinated hydrocarbon solvent; and
   i. recovering vinblastine from the chlorinated hydrocarbon solvent.

3. A process as claimed in claim 2, wherein the starting mixture of diindole alkaloids is in the form of sulfate salts.

4. A process as claimed in claim 2, wherein methanol or ethanol is used to dissolve the starting alkaloid salt mixture.

5. A process as claimed in claim 2, wherein benzene is used as the said hydrocarbon-type solvent.

6. A process as claimed in claim 2, wherein an aqueous phosphate buffer solution having a pH-value of 4.0±0.1 is used for extracting the residual diindole alkaloids from the said evaporation residue.

* * * * *